(12) United States Patent
Zurkirchen et al.

(10) Patent No.: US 8,330,067 B2
(45) Date of Patent: Dec. 11, 2012

(54) METHOD AND APPARATUS FOR THE OPTICAL INSPECTION OF WORKPIECES

(75) Inventors: Karl Zurkirchen, Lucerne (CH); Christoph Stohler, Lucerne (CH); Nicolai Ruedi, Chur (CH); Othmar Amrein, Eschenbach (CH)

(73) Assignee: Sontec AG, Hochdorf (CH)

( * ) Notice: Subject to any disclaimer, the term of this patent is extended or adjusted under 35 U.S.C. 154(b) by 31 days.

(21) Appl. No.: 12/913,451

(22) Filed: Oct. 27, 2010

(65) Prior Publication Data

US 2011/0100883 A1 May 5, 2011

(30) Foreign Application Priority Data

Nov. 2, 2009 (EP) .................................... 09174787

(51) Int. Cl.
*B07C 5/00* (2006.01)

(52) U.S. Cl. ........ 209/577; 209/684; 209/686; 209/938; 209/939

(58) Field of Classification Search .................. 209/577, 209/684, 685, 938, 939
See application file for complete search history.

(56) References Cited

U.S. PATENT DOCUMENTS

| | | | | |
|---|---|---|---|---|
| 2,132,447 A * | 10/1938 | Stout | ............................... | 209/3.1 |
| 3,756,402 A * | 9/1973 | Wagers et al. | ................. | 209/541 |
| 3,991,882 A * | 11/1976 | Fahnestock et al. | ........... | 209/588 |
| 4,437,559 A * | 3/1984 | Ackley et al. | ............. | 198/397.04 |
| 4,593,190 A * | 6/1986 | Kawasaki et al. | ......... | 250/223 R |
| 4,673,077 A * | 6/1987 | Taniguchi | ...................... | 198/393 |
| 4,908,092 A * | 3/1990 | Koibuchi | ....................... | 156/556 |
| 5,259,716 A * | 11/1993 | Hoshino et al. | .......... | 414/223.01 |
| 6,064,759 A | 5/2000 | Buckley et al. | | |
| 7,036,655 B2 * | 5/2006 | Schafer | ....................... | 198/459.2 |
| 2007/0065945 A1 * | 3/2007 | Sigrist | .............................. | 436/43 |

FOREIGN PATENT DOCUMENTS

| | | |
|---|---|---|
| DE | 196 13 233 A1 | 10/1997 |
| JP | A-02-067947 | 3/1990 |
| JP | B-06-041925 | 6/1994 |
| JP | A-2001-201457 | 7/2001 |
| WO | WO 01/09013 A1 | 2/2001 |

OTHER PUBLICATIONS

European Search Report issued in European Patent Application No. 09 17 4787 dated Mar. 5, 2010 (with translation).

* cited by examiner

*Primary Examiner* — Terrell Matthews
(74) *Attorney, Agent, or Firm* — Oliff & Berridge, PLC

(57) ABSTRACT

The apparatus, which serves for the optical inspection of workpieces, comprises a transport device driven by a drive unit, which transport device is supplied with workpieces delivered by a loading device, which workpieces are transported by the transport device to at least one inspection position, where an optical inspection is performed, and further to at least one discharge position, where the inspected workpieces are selectively extractable by a discharge device. According to the invention, a plurality of transparent receiving bodies are firmly mounted or rotatably supported on the transport device, each of the receiving bodies comprising a recess, into which the workpieces can be inserted individually or in groups, and wherein an inspection radiation can be guided through each receiving body in order to image the held workpieces.

15 Claims, 7 Drawing Sheets

Figure 1:
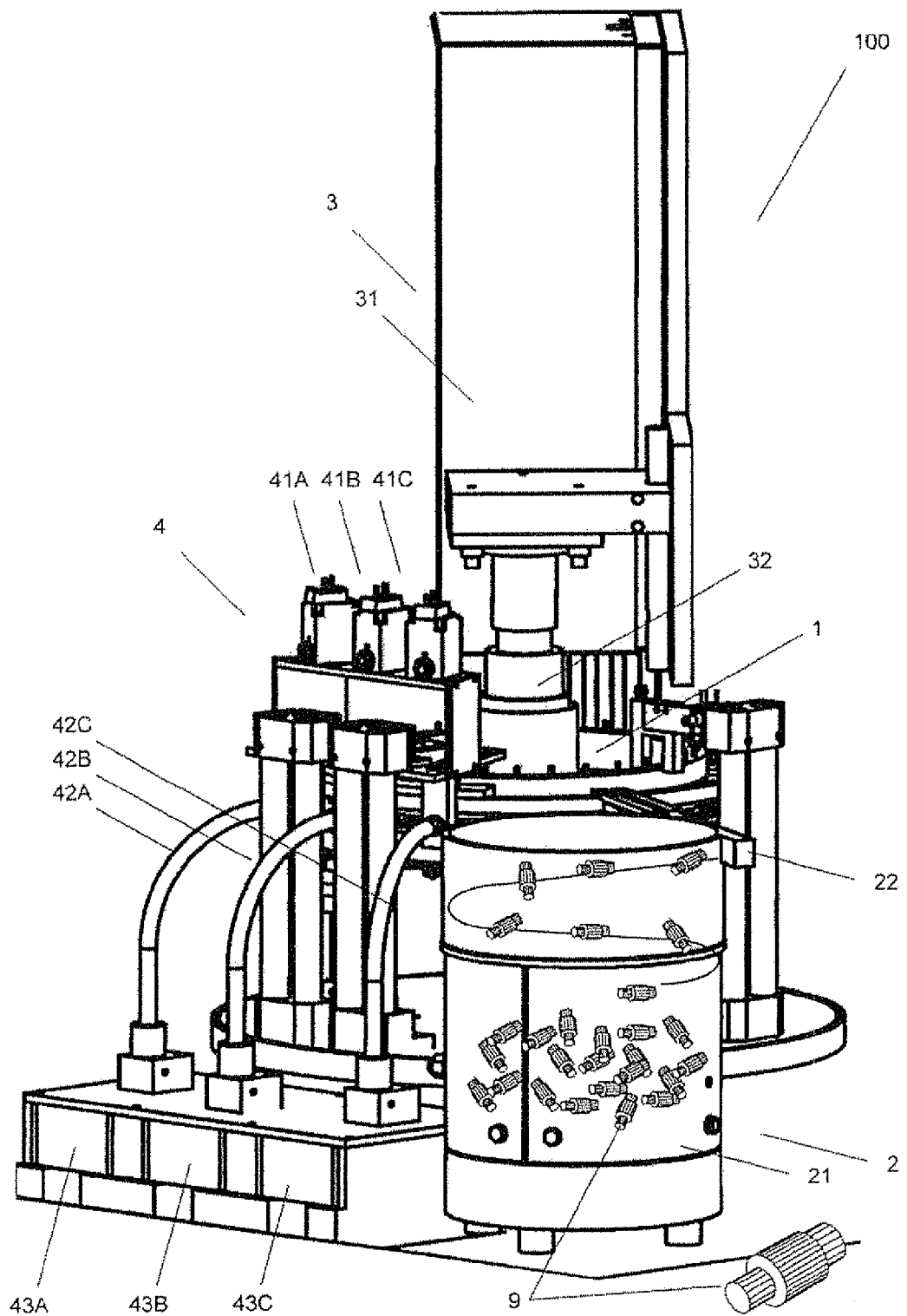

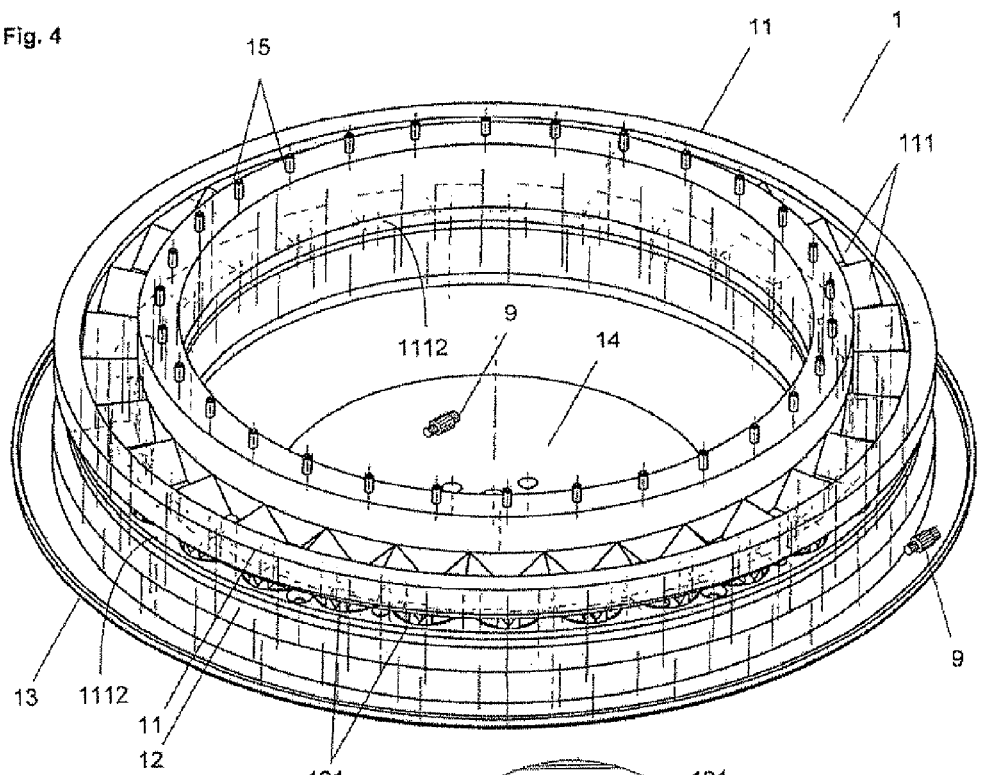
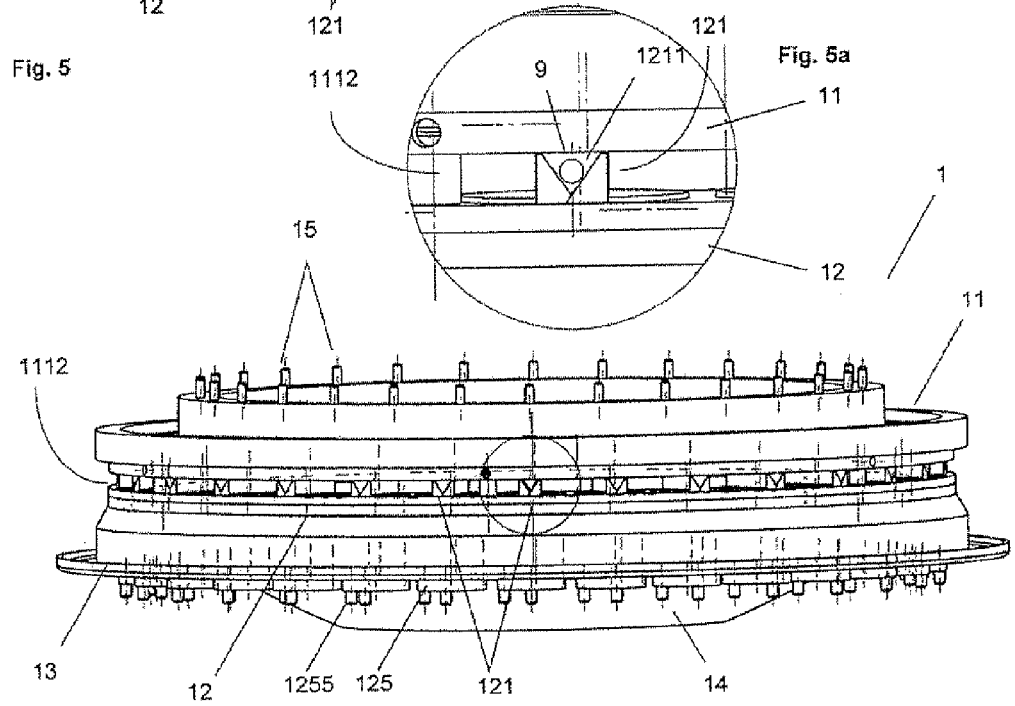

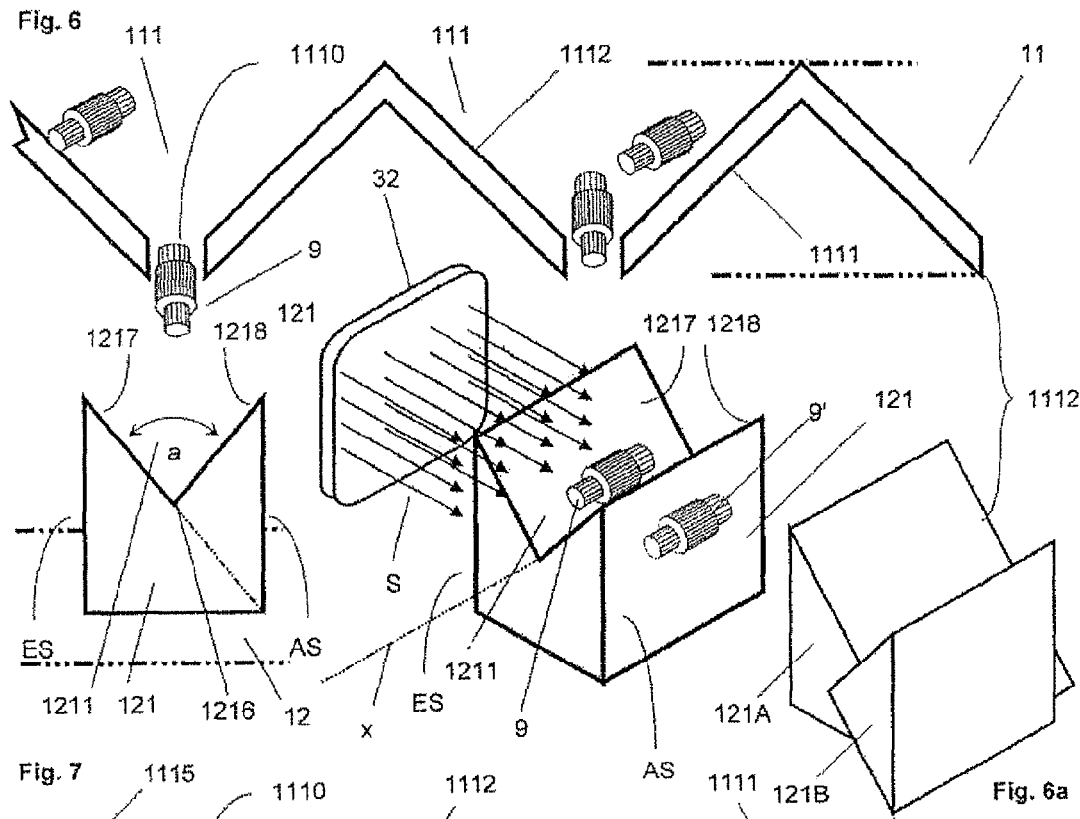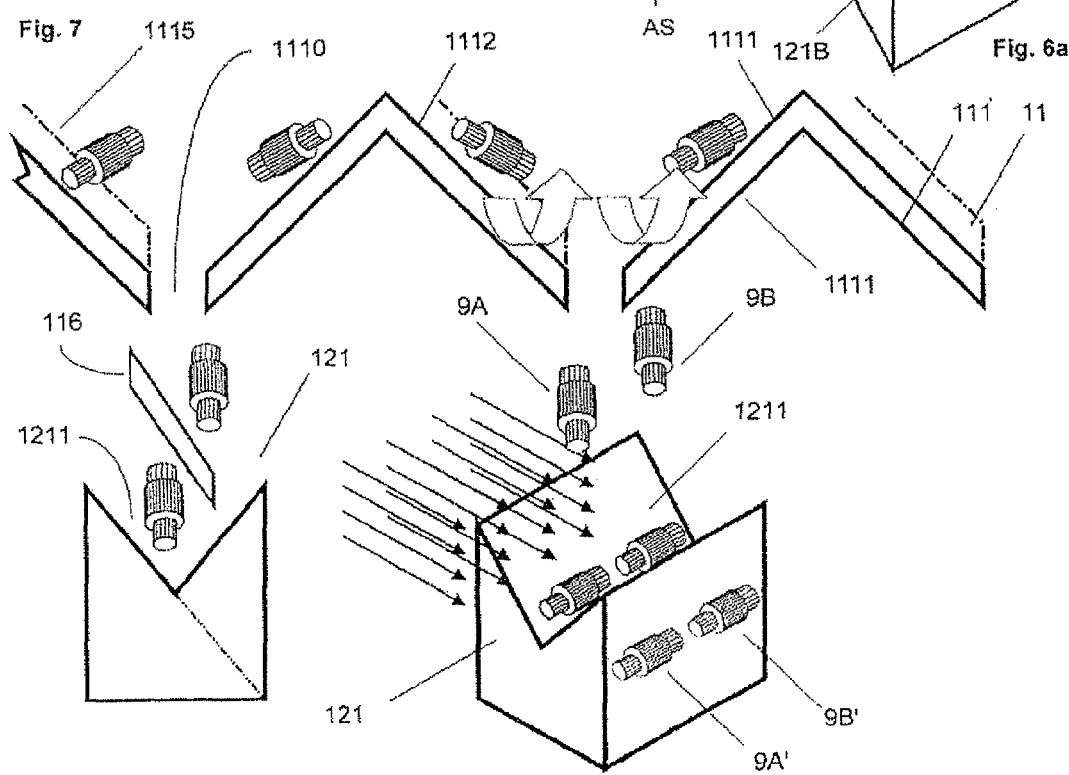

METHOD AND APPARATUS FOR THE OPTICAL INSPECTION OF WORKPIECES

The invention relates to an apparatus and a method for the optical inspection of workpieces, which, scattered on a transport device, can be transported from a receiving position to at least one inspection position and further to at least one dispensing position.

Such an apparatus, which serves for the optical inspection of workpieces, is described for example in [1], WO 01/09013 A1. With this device workpieces that require inspection are individually set up on a closed loop conveyor belt that serves as transport device and that transports the workpieces along an endless transport track. The workpieces held in recesses of the conveyor belt are then measured by means of optical measuring devices that are positioned along the transport track. The workpieces supplied are forwarded via a disc that peripherally is provided with recesses, that is rotatably supported and that is driven by a motor, to the recesses provided in the conveyor belt and are held by the conveyor belt in a desired alignment. By individualising the workpieces disturbing overlapping of neighbouring workpieces can be avoided. After the end of the inspection the workpieces are removed from the conveyor belt and, depending on the result of the inspection, put into a first box that is provided for faultless workpieces or into a second box that is provided for flawed workpieces.

Disadvantageous with this solution is i.a., that the recesses in the conveyor belt must be adapted to the workpieces, so that they are securely held. The apparatus is therefore not flexible and can only process a single type of workpieces. Further, for the insertion of the workpieces a device is required that is synchronised with the conveyor belt, so that the recesses in the conveyor belt can be charged with a defined timing. A disc provided for this purpose comprises air channels, through which the workpieces are sucked in and released in the same process cycle. The individual process steps, particularly the insertion of a workpiece into the conveyor belt, require relatively long time periods so that only a relatively low throughput can be achieved. Further, with this apparatus disturbances must be taken into account if the workpieces are not positioned with highest precision. Disadvantageous is further, that very small workpieces can not be processed with this apparatus.

From [2], DE19613233A1, an apparatus is known that instead of a conveyor belt uses a rotary disk as a transport device, which holds the workpieces peripherally and transports them along a circular transport track. In order to hold the workpieces stably in a desired position, it is foreseen that the workpieces adhere to the transport device. For this purpose, the transport device is provided with permanent magnets, which attract the ferromagnetic workpieces. With this apparatus only ferromagnetic workpieces can be held and measured. However, the workpieces can take different positions, so that a desired reproducibility of the measurement conditions is not reached. In view of the use of permanent magnets it must be taken into account that difficulties can result in the process steps of picking up or discharging the workpieces. The separation of the workpieces from the transport device may require a relatively high force so that the discharge of the pieces can not easily be controlled. In view of the difficulties that may occur when using magnetic forces, also with this apparatus a desired throughput can scarcely be achieved. Further, it is to be expected that the control of magnetic forces becomes more difficult with decreasing dimensions of the workpieces so that also with this apparatus very small workpieces cannot be inspected. Further, it is expected that the magnetisation of parts of the apparatus may change. In particular it is possible that parts of the apparatus or tools unintentionally get magnetised so that problems may result with the handling of the workpieces With the apparatuses of [1] and [2] it is further to be noted, that the optical measurement of the workpieces is impaired by parts of the transport device that directly adjoin the workpieces, so that higher efforts are required for image processing and the desired measurement precision and resolution may not be achieved. In particular the neighbouring parts of the transport device may cause disturbing light reflections or shadowing effects, which may lead to faulty measurements.

The present invention is therefore based on the object of providing an improved method and an improved apparatus for optically inspecting workpieces.

In particular an apparatus shall be created with which a higher throughput can be achieved.

The apparatus shall enable inspection of large and extremely small workpieces, which can vary in size during the measurement process in a relatively large range. Particularly, it shall be possible to inspect workpieces, whose dimensions are in the range of 1 mm or below. Further, it shall be possible to inspect workpieces that are made from any material. It shall be possible to measure workpieces comprising a head, such as screws, and workpieces without head, such as threaded rods.

In order to facilitate measurement, it shall be possible to precisely position the workpieces, particularly rotation-symmetric workpieces, on the transport device, so that the workpieces can take preferably only one exactly defined position. For the precise measurement, it shall be possible to individualise the workpieces with little effort. Further, it would be desirable, that groups, each with at least two individualised workpieces, can be forwarded to the inspection position and can be measured as a group.

The measurement of the workpieces shall be done with high precision and shall not be impaired in particular by parts of the transport device.

Furthermore, the handover of the workpieces to the transport device shall not be bound to a specific duty cycle. Instead it shall be possible to handover the workpieces continuously to the transport device by means of a conveyor device, to which the workpieces are fed unordered.

It shall be possible to perform measurement and inspection of the workpieces "on the fly", i.e. without stopping the transport device, so that a maximum throughput of workpieces can be achieved.

Furthermore, the apparatus shall be compact in construction and take only a little space. Further, it shall be possible to control the apparatus, which shall cause only reduced maintenance requirement, with little effort.

This object is achieved with a method and an apparatus, which comprise the features defined in claim 1 and claim 6 respectively. Preferred embodiments of the invention are defined in further claims.

The apparatus, which serves for the optical inspection of workpieces, comprises a transport device driven by a drive unit, which transport device is supplied with workpieces delivered by a loading device, which workpieces are transported by the transport device to at least one inspection position, where an optical inspection is performed, and further to at least one discharge position, where the inspected workpieces are selectively removed by a discharge device.

According to the invention, a plurality of transparent receiving bodies are firmly mounted or rotatably supported on the transport device, each of the receiving bodies comprising a recess, into which the workpieces can be inserted individually or in groups, and wherein an inspection radiation can be guided through each receiving body in order to image the held workpieces.

The workpieces can advantageously be inserted into the recesses of the transparent receiving bodies and removed therefrom again. Within the recesses the workpieces are automatically held stable. Preferably, recesses are selected, that comprise the form of a triangular prism, of which two sides are formed by the receiving body. Through the third side of the triangular prism, which can be kept open, the workpieces can enter the recess as far as they reach the other two sides of the triangular prism. Depending on their dimensions the workpieces are held at a specific height within the recess. Viewed from the side, the workpieces appear to be floating within the recess or within the receiving body respectively. Inspection radiation, which is guided through the receiving body, is therefore reflected by the inserted workpiece only and can otherwise pass unobstructed through the receiving body. The workpiece can therefore be imaged without disturbing environmental influences.

It is further to be noted that by designing the recess as a triangular prism a tolerance range is created, within which the supplied workpieces are engaged and centred.

The transparent receiving bodies, which preferably are made of glass or plastic, are preferably designed as multi-sided straight prisms. For example, a five sided prism is provided, in which a recess is incorporated that comprises the form of a triangular prism. However, incorporating a recess into a glass- or plastic body also involves difficulties, such as requiring casting or compression moulding of a corresponding body. Therefore, in a preferred embodiment, a receiving body is used that is composed of at least two parts. The receiving body can be created particularly advantageous by combining two triangular prisms with one another, e.g. by mechanical or chemical means. The design of the recess as a triangular prism is particularly advantageous. However, it is also possible to use receiving bodies with non-planar side surfaces. This is for example in peripheral regions advantageous, which have no influence on the measurement, but serve for engaging and guiding the workpieces.

Therefore, the transparent receiving bodies, which can be designed differently, fulfil several functions optimally.

The workpieces can be transferred by gravity into the recess and are securely engaged and held therein. Here, a relatively high variance is allowed, i.e., the individual workpieces are allowed to enter the recess at different positions, which are typically larger by a multiple than the workpieces. A timed handover by means of controlled device elements is not required. The workpieces need therefore not to be grasped and handed over to the receiving bodies. This eliminates major problems that have scarcely or only with high efforts been solved with known apparatuses. In particular, problems are avoided, which become more apparent when using workpieces with reduced dimensions. Since it is not required to grasp and handover the workpieces individualised to the transport device, it is possible to supply and inspect workpieces, whose dimensions are in the millimetre range or below. According to the invention, workpieces of micromechanical products can be inspected, which could be examined before only with high efforts, e.g. under the microscope.

Further, the workpieces can be thrown in to the recesses of the receiving bodies, while the receiving bodies are moved. For this reason a continuously running process can be achieved. Likewise, the workpieces, which do not adhere to the receiving bodies, can be removed and transferred to a corresponding storage unit with little effort, e.g. by means of air pressure or by gravity after turning the receiving bodies.

Further, the inventive solution allows an advantageous synchronisation of the workpieces with the receiving bodies, which workpieces are supplied for example by means of a helical conveyor at different time intervals. For this purpose above each receiving body an intake funnel is provided, into which the workpieces are thrown. Earlier or later arriving workpieces are centred and transferred through the outlet opening of the intake funnel into the recess of the below positioned receiving body, which can receive the workpieces in a sufficiently large tolerance range as well. The whole process, which leads to an accurate loading of the receiving bodies, requires no auxiliary means and no control processes. Further, the loading process can run continuously, without providing timed process steps.

In a preferred embodiment, the loading process is controlled by the inspection device only, which determines, whether two or more workpieces are present in the recesses. In the event that incorrect loading occurs seldom, such incorrect loading is ignored. If the incorrectly loaded workpieces cannot be measured, then they are classified as undefined, removed and again supplied to the loading device. However, if unloaded or overloaded receiving bodies occur more often, then a corresponding correction signal is sent to the loading device in order to correct the conveyor speed accordingly.

Within the recesses of the receiving bodies the workpieces virtually take a floating position, so that they can be imaged free from disturbing optical effects. The optical measurement is performed with high precision and line sharpness, so that deficiencies of the workpieces can precisely be detected. Further, a plurality of workpieces can simultaneously be optically recorded, if they do not overlap in the recess. This can be achieved, by providing guiding elements above the receiving bodies, e.g. in the intake funnels, which guide the workpieces in the one or the other direction.

The transport device allows firm mounting or rotatably supporting as well as the transport of the transparent receiving bodies along a circular or partially linear transport track that forms a closed loop. For this purpose the transport device can be designed e.g. as a rotor, as a ring, as a belt or as a chain. In preferred embodiments the receiving bodies are supported in such a way, that they can perform movements in a plane or in space, so that they can receive, present and discharge workpieces at any desired position. This can advantageously be implemented by providing control elements along the transport track, such as curves or a slotted guiding member, which grasp and turn the receiving bodies. For this purpose, the receiving bodies are preferably arranged on a holding device, which is held in the transport device and is rotatable between at least two positions. It is preferably provided that the holding device, which is supported on a point or along an axis, can be fixed at each of these positions by a mechanical or magnetic element. Thus, the receiving bodies can take a precisely defined position at a loading position, at least one inspection position and at least one discharge position. Preferably the transport device comprises a receiving ring, on which identical receiving bodies are firmly mounted or rotatably supported in equal distances.

A synchronisation ring with the described intake funnels is preferably arranged above the receiving ring. The use of the receiving ring and the synchronisation ring allows a compact set up of the transport device, which not only provides a transport function, but also the synchronisation function and the handling function, since the workpieces are exposed at the inspection position in a desired position. Preferably, the synchronisation ring and the receiving ring are separated by distance elements from one another, so that a free interspace results, into which the receiving bodies are projecting at least so far, that their recesses with the workpieces held therein are positioned within the interspace and can optically be detected. Thereby, a light source or an optical deflection element is preferably provided on the inner side and a recording device or an optical deflection element is provided on the outer side of the receiving ring. This has the advantage, that the inspection radiation can be guided from only one centrally arranged light source to a plurality of inspection positions. E.g., the workpiece held by the receiving body can be aligned at a first inspection position perpendicularly and at a second inspection position in parallel to the inspection radiation. The inspection radiation is preferably guided via optical elements along a beam path, that describes a "U", with the lower side running within the interspace between the synchronisation ring and the receiving ring. In this way, the inspection device can be arranged in free space above the transport device, while the space at the height of the transport device is kept free for handling the workpieces.

Figure 2:
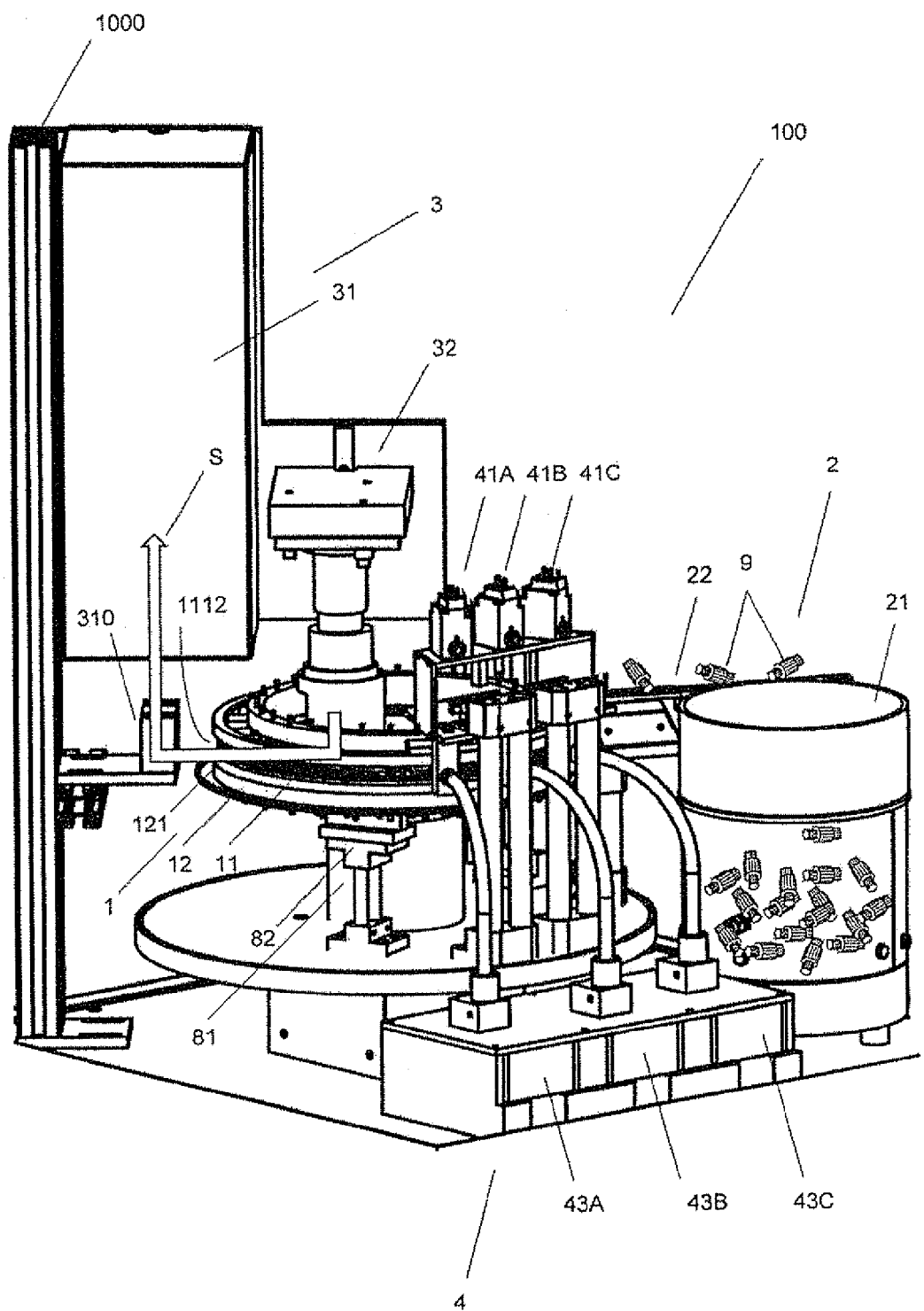
Figure 3:
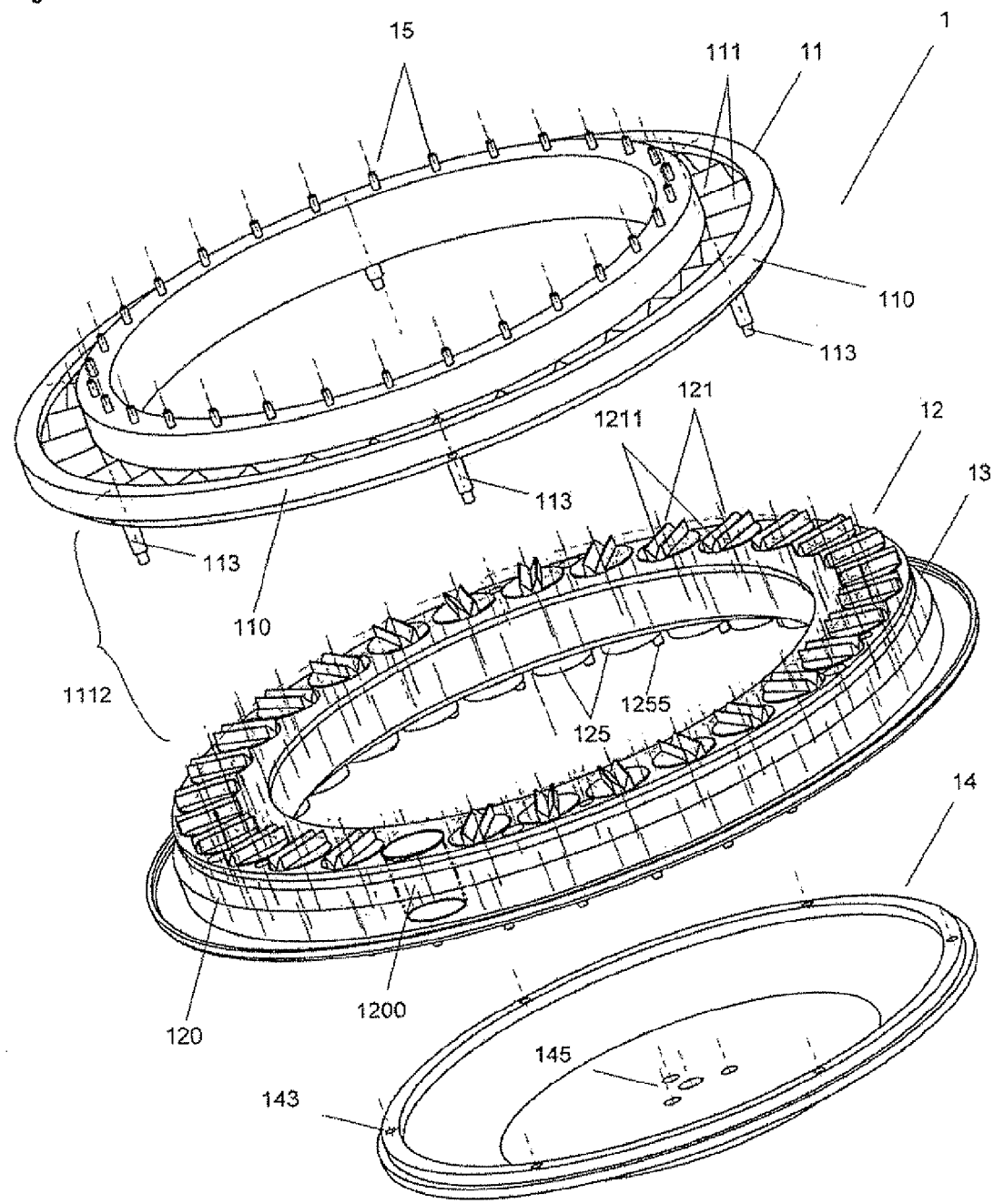
Figure 8:
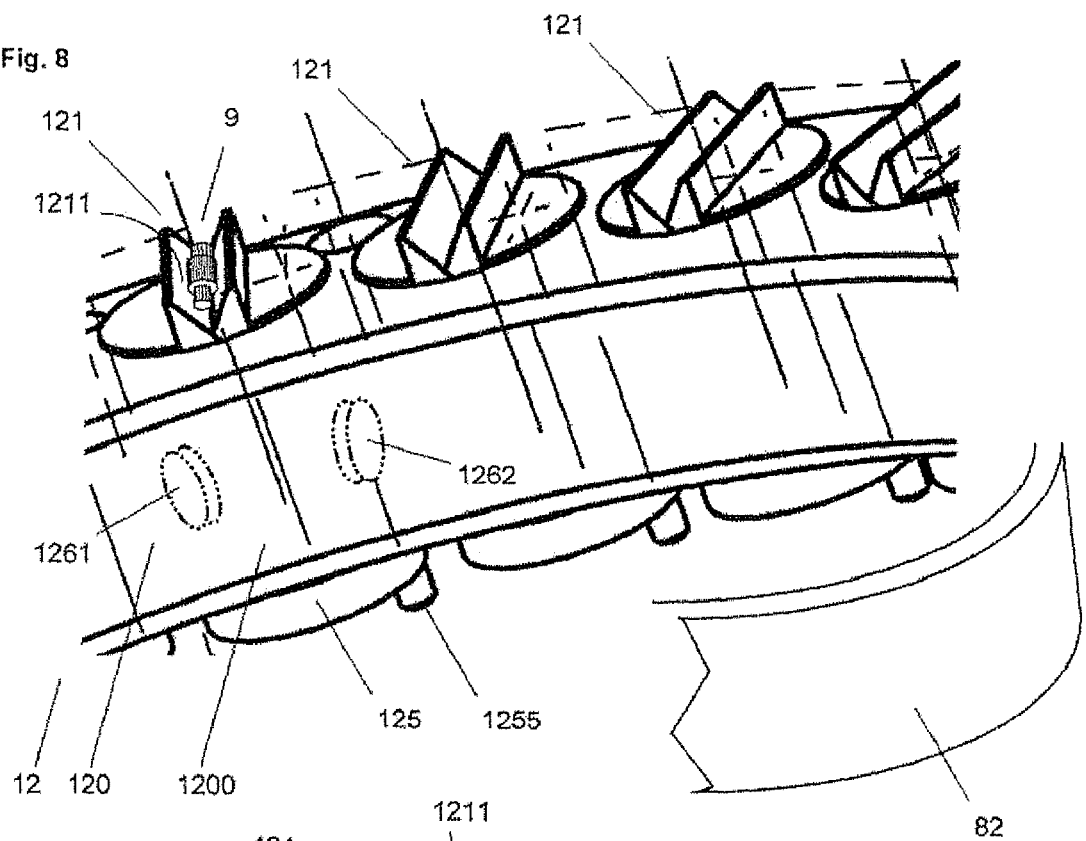
Figure 9:
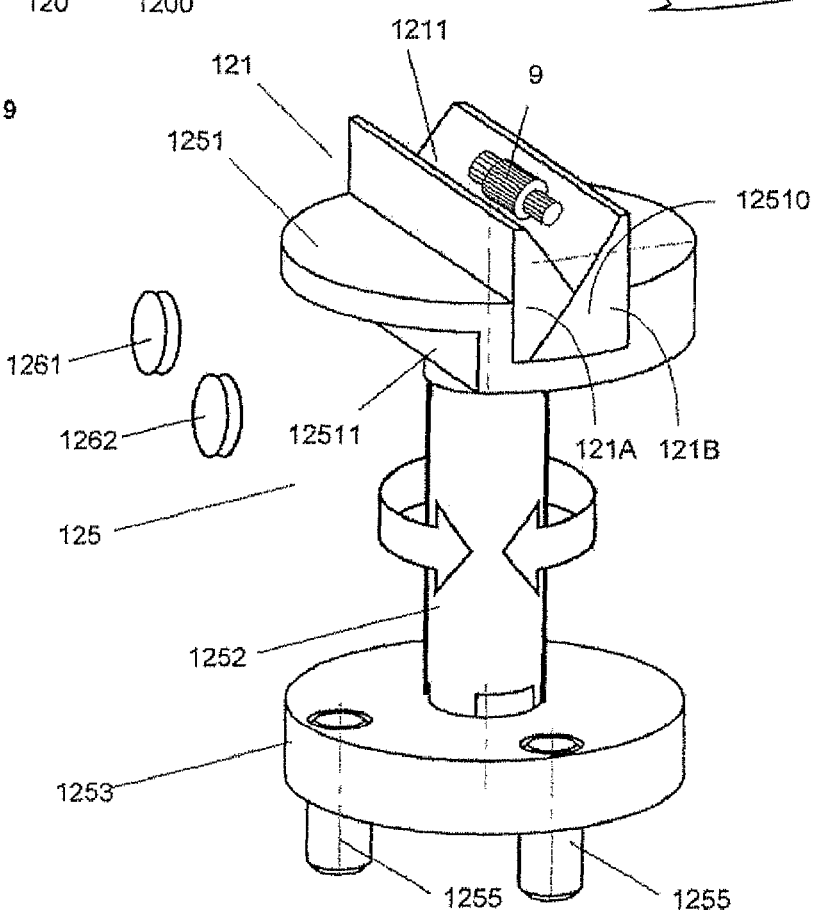
Figure 10:
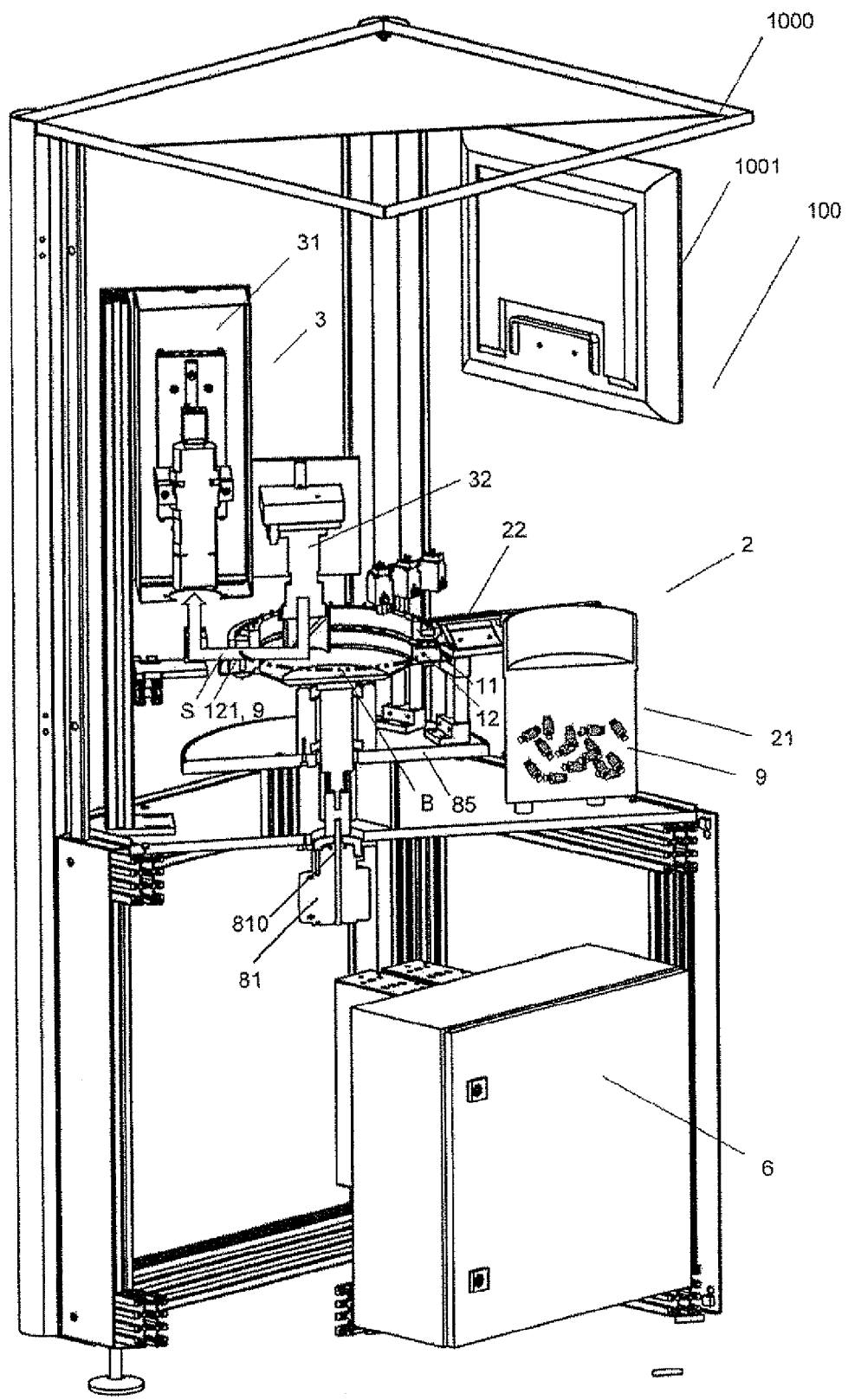

Below the invention is described in detail with reference to the drawings. Thereby show:

FIG. 1 an inventive apparatus 100 with a loading device 2, with which workpieces 9 that require inspection are provided to a transport device 1 that is designed as a rotor and that transport the workpieces 9 to an inspection device 3 and further to a discharge device 4;

FIG. 2 the apparatus 100 shown in FIG. 1 with a view onto the transport device 1, which comprises a synchronisation ring 11 comprising intake funnels 111 and a receiving ring 12, on which transparent receiving bodies 121 are provided, which serve for receiving the workpieces 9 that require inspection;

FIG. 3 the transport device 1 of FIG. 2 with the synchronisation ring 11 and the receiving ring 12, which are screwed to a mounting disk 14, which is connected to the drive shaft 810 of the drive unit 81;

FIG. 4 the assembled transport device 1 of FIG. 3 seen from above;

FIG. 5 the assembled transport device 1 of FIG. 3 seen from the side;

FIG. 5a a section of FIG. 5 with the exposed part of a receiving body 121, which comprises a recess 1211, in which a workpiece 9 is held;

FIG. 6 a schematic view of the synchronisation ring 11 of FIG. 5 with receiving bodies 121 arranged below, which in a preferred embodiment are rotatable into defined positions, in which they can be loaded, exposed to radiation or discharged;

FIG. 6a two triangular prisms 121A, 121B, which are assembled to a five sided prism forming a receiving body 121;

FIG. 7 a preferred embodiment of the synchronisation ring 11, which is provided in addition with guiding elements 1115, which allow disposing two or more workpieces 9 sorted into a recess 1211 of the receiving body 121;

FIG. 8 a part of the receiving ring 12, which comprises cylindrical openings 1200 and holding devices 125 provided with a receiving body 121 rotatably supported in each cylindrical opening 1200;

FIG. 9 a holding device 125 of FIG. 8 provided with a two-part receiving body 121, which is held within the opening 1200 rotatable within an angle of 90° from a first to a second stopper and held at each stopper by a magnet 1261, 1262; and FIG. 10 a sectional view of the apparatus 100 of FIG. 1 after the installation in a housing 1000.

FIG. 1 shows an inventive apparatus 100, which comprises a loading device 2, a transport device 1, an inspection device 3 and a discharge device 4.

By means of the loading device 2, which in the present embodiment comprises a helical conveyor 21 and a linear conveyor 22 following thereto, workpieces 9 are forwarded to the transport device 1. In principle, various conveyor systems, such as helical conveyors, centrifugal conveyors or tube conveyors, can be applied, which deliver workpieces 9 with a dedicated duty cycle or in different time intervals to the transport device 1. Helical conveyors have the advantage, that workpieces 9 provided in bulks can be grasped and serially conveyed, so that always a serial handover to the transport device 1 with a selectable throughput is achieved.

With the apparatus 100, workpieces 9 of any size can be inspected, e.g. parts of micromechanical devices or parts of a clock unit. Further, workpieces 9 can be inspected, which are made from any material. In FIG. 1 rotation symmetric workpieces 9 are shown, which can precisely and, if required, in different alignments, be measured.

The supplied workpieces 9 are forwarded by the transport device 1 to an inspection device 3 that comprises a light source 32 and a recording device 31 and that is controlled by a computer. The inspection device 3 performs an optical examination of the supplied workpieces 9 and discriminates between good and deficient workpieces 9 and preferably sorts out undefined workpieces 9, which are rerouted into the inspection process. In the event that for example, based on different causes, no clear examination result is achieved, then the concerned workpieces 9 are classified as undefined. This may happen for example, if the workpieces 9 overlap one another within the recess 1211 of the receiving bodies 121.

After the inspection the workpieces 9 are forwarded to a discharge device 4, which separates the inspected workpieces 9 on three different discharge positions selectively from the transport device 1. For this purpose, air pressure is selectably guided from one of three valves 41A, 41B, 41C to a discharge position, from where the workpiece 9 lying there, which is either good, deficient or undefined, is blown into one of three transfer hoses 42A, 42B, 42C and is guided to a corresponding storage unit 43A, 43B, 43C, in which good, deficient or undefined workpieces 9 are stored. The discharge of the workpieces 9 from the receiving bodies 121 can also be performed in another way, e.g. by mechanical elements or by means of gravity, by turning the receiving bodies downward.

FIG. 2 shows the apparatus 100 of FIG. 1 with a view to the transport device 1, which comprises a synchronisation ring 11 provided with intake funnels 111 and a receiving ring 12, on which transparent receiving bodies 121 are rotatably supported, which serve for receiving the workpieces 9 that require inspection. The transport device 1 is designed as a compact rotor, which is driven by a motor 81 (see also FIG. 10). The light source 32 protrudes into the rotor and provides an inspection radiation S, which is guided through between the synchronisation ring 11 and the receiving ring 12 and via an optical deflection element, such as a prism or a mirror, to the receiving optical system of a camera 31 (see also FIG. 10).

Below, the transport device shown in FIGS. 1 and 2 is described more closely.

FIG. 3 shows the synchronisation ring 11, the receiving ring 12 and the mounting disk 14 of the transport device 1 before the parts are assembled. The synchronisation ring 11 comprises a ring body 110, along which intake funnels 111 with outlet openings on the lower side form a closed loop of a funnel chain. At the lower side of the ring body 110 distance elements 113 are provided, which are supported on the receiving ring 12. By this measure an interspace 1112 is always kept free between the synchronisation ring 11 and the receiving ring 12. The synchronisation ring 11 and the receiving ring 12 are screwed to a mounting disk 14, which comprises threaded bores 143 that serve for receiving mounting screws and which is connected to the drive shaft 810 of the drive unit 81 by means of mounting elements 145 (see FIG. 10).

The receiving ring 12 comprises a ring body 120 with cylindrical openings 1200, into which holding devices 125 are inserted that support the transparent receiving bodies 121. The receiving bodies 12, each of which comprising a recess 1211 for receiving a workpiece 9, are arranged below an intake funnel 111, so that each receiving body 12 is assigned to an intake funnel 111. Workpieces 9 that are supplied to the intake funnels 111 are therefore always forwarded to the receiving bodies 121 arranged below. The holding devices 125 are rotatably supported within the openings 1200 so that the recesses 1211 in the receiving bodies 12 can be aligned in accordance with the outlet openings 1110 of the intake funnels 111 lying above (see FIG. 6). By the corresponding alignment of the recesses 1211 it is assured that the workpieces 9 delivered from the intake funnels 111 can securely been caught. Individual workpieces 9 that are not held in the receiving bodies 121 fall either inside into the mounting disk 14 or outside into a flange ring 13 that is mounted on the receiving ring 12. Thus, misguided workpieces 9 can correctly be caught and can be rerouted to the loading device 2 without causing disturbances.

Turning the holding devices 125 is performed with control elements 1255, pivots or cams, which are provided on the holding device 125 and which for example are engaged and guided in a control curve 82, which is arranged below the receiving ring 12. With the control curve 82 shown in FIG. 2, the holding devices 125 are turned into a suitable position before reaching the discharge positions. Turning the holding devices 125 with the receiving bodies 121 is therefore done automatically when turning the transport device 1, for which reason alternative drive elements and control elements are not required.

Preferably, the receiving bodies 121 are turned with the main axis x of the recess 1211 before reaching the at least one loading position, the at least one inspection position and the at least one discharge position by 90° perpendicularly or in parallel to the radius of the receiving ring 12, if the desired alignment is not already present.

To ensure that the inspection processes and the discharge processes are always performed when the receiving bodies 12 are at the corresponding positions, the synchronisation ring is provided with marking elements 15, which are detected e.g. by an electric eye when reaching a specific position.

FIG. 4 shows the assembled transport device 1 of FIG. 3 seen from above. FIG. 5 shows the assembled transport device 1 of FIG. 3 seen from the side.

FIG. 5a shows a section of FIG. 5 with the exposed part of a receiving body 121 comprising the recess 1211, in which a workpiece 9 is held. The recess 1211 of the receiving body 121 lies in the interspace 1112 between the synchronisation ring 11 and the receiving ring 12 and lies at an inspection position therefore in the optical path of the inspection radiation S.

FIG. 6 shows a schematic view of the synchronisation ring 11 of FIG. 5 with the intake funnels 111, below which the receiving ring 12 with the transparent receiving bodies 121 is arranged. The recess 1211 of each receiving body 121 is positioned directly below the outlet opening 1110 of an intake funnel 111, so that workpieces 9, which were delivered by the loading device 2, are falling from the outlet opening 1110 of the intake funnel 111 directly into the recess 1211 of the corresponding receiving body 121 and are held there centred. In the shown embodiment, each intake funnel 111 comprises a front side 1111 and a backside 1112, which ensure that workpieces 9 that arrive earlier or later are guided through the outlet opening 1110 to the receiving bodies 12 and are thus synchronised with the receiving bodies 12.

FIG. 6 shows further the transparent receiving bodies 121 in a preferred embodiment, in which they comprise the form of a five sided prism. This prism can be manufactured from glass or plastic by incorporating a triangular prism into a four sided prism. This however involves considerable efforts. Further, in this way, the inner angle 1216 of the prism can be manufactured only with high effort with the desired precision.

However, as shown in FIG. 6a, the receiving body, i.e. the five sided prism 121 can be composed most advantageously by a larger and the smaller triangular prism 121A, 121B, that are connected to one another for example by means of an adhesive. To ensure that the triangular prisms 121A, 121B can be connected directly adjoining one another, the adhesive is preferably inserted into slots or grooves that are incorporated into the mating surfaces of the triangular prisms 121A, 121B.

Further, FIG. 6 shows a spatial view of a receiving body 121 having a recess 1211 into which a workpiece 9 has been disposed. The receiving body 121 is exposed on the inlet side ES to the inspection radiation S of the light source 32, which inspection radiation S penetrates the receiving body 121 and the recess 1211 as a bundle of light beams that are aligned in parallel. The workpiece 9 is imaged or mapped on the outlet side AS of the receiving body 121 by the exiting inspection radiation S, which is further guided to the optical system of the camera 31. It is symbolically shown that the image 9' of the workpiece 9 is floating and is not impaired by parts of the device. The image 9' of each workpiece 9 has a high resolution and is free from optical disturbances. With the analysis of the image 9' performed by the inspection device the dimensions and thus the status of the workpieces 9 can precisely be determined.

Preferably, an opening angle (a) of the recess 1211 is selected in such a way that the workpiece 9 is held by the sides 1217, 1218 of the recess 1211 in the half height of them and thus with a distance to the lower angle 1216. The lower angle 1216 of the recess 1211 does therefore not optically appear as a disturbance. In the contrary, the workpiece 9 is automatically centred and either in a first or second position aligned in parallel to the main axis of the receiving body 121 and thus in parallel to the lower angle 1216. By the fact that always the same alignment of the received workpieces 9 is reached, the measurement efforts are reduced.

Further, the workpieces 9 are held in the recess 1211 from two sides, wherefore the workpieces 9 can not leave their position when the transport device 1 is rotated or when the receiving bodies 121 are turned. Therefore it can be ascertained that the receiving bodies 121 are always aligned tangentially to the transport device 1 between the loading position and the discharge position, so that the effect of the centrifugal forces is neutralised. This tangential alignment is further the preferred orientation of the receiving bodies 121 at the inspection position. At a discharge position however air pressure can be introduced from one of the base sides of the triangular prism so that the examined workpiece 9 is ejected.

FIG. 7 shows a preferred embodiment of the synchronisation ring 11, which is provided in addition with guide elements 1115, which allow disposing two or more workpieces 9 sorted in the recess 1211 of the receiving body 121. A workpiece 9 that is arriving earlier is guided by the first edge 1111 of the intake funnel 111 in the one direction and a workpiece 9 that is arriving later is guided by the second edge 1112 of the intake funnel 111 in the other direction, so that earlier or later arriving workpieces 9A, 9B are radially separated from one another and are separately disposed in the recess 1211 of the receiving body 121. FIG. 7 shows that for two workpieces 9A, 9B, which are positioned in such a way, two separate images 9A', 9B' can be obtained during optical inspection, which can be analysed with little effort. By transferring two workpieces 9A, 9B to a receiving body 121 the throughput can be doubled.

The separation of the workpieces 9, which are supplied by one or more loading devices 2, can be achieved in several ways. It is possible to throw workpieces 9 separated into the synchronisation ring 11. Further, two are more intake funnels 111 can be provided in parallel to one another. Alternatively an intake funnel 111 can have a plurality of outlet openings 1110. Still further, a separation element 116 can be provided between the intake funnel 111 and the receiving body 121.

In principle, the throughput can further be raised. Two recesses 1211 can be provided in the receiving bodies 121. For example a recess 1211 positioned higher and a recess 1211 positioned lower can be provided, so that the workpieces disposed therein are separated in height.

FIG. 8 shows a part of the receiving ring 12, which comprises cylindrical openings 1200, preferably stepped bores, in each of which a holding device 125 is rotatably supported. The holding devices 125 are provided with a cam-like control element 1255, which is interacting along the transport track B with a control curve 82 (see also FIG. 2), in order to align the holding device 125 as required.

The holding devices 125, shown in FIG. 9 in spatial view, comprise a head piece 1251 and a foot piece 1253, which are connected to one another by a shaft 1252 lying therebetween. The head piece 1251 is provided on the upper side with a receiving channel 12510, into which a two-parted receiving body is inserted. At the lower side the head piece 1251 comprises a straight running stopper 12511, which in a first and in a second turning position of the holding device 125 is abutting the ring body 120 and can be fixed there with magnets 1261, 1262. The foot piece 1253 is provided with two control elements 1255, which can interact with at least one control curve 82.

FIG. 10 shows a sectional view of the apparatus 100 of FIG. 1 after the installation into a housing 1000. It can be seen that the apparatus 100 requires only little space, wherefore further devices, such as a control and computing device 6 as well as a monitor 1001 can easily be integrated.

The apparatus 100 is mounted on a plate 85, which supports auxiliary elements, such as supports for the control curves 82 and the linear conveyor 22. Below the plate 85, a drive motor is provided, whose drive shaft 810 is coupled to the transport device 1. In this sectional view the path of the inspection radiation S, which radially traverses the transport device 1, can well be seen.

In view of the efficient use of the available space two or more transport devices 1 can advantageously be arranged above one another and operated according to the invention.

In the drawings, the transport device 1 is shown as a rotor. However, the inventive solution is not limited to this embodiment. The transport device 1 can also be designed as a closed loop linear conveyor, e.g. as a belt or a chain, which guides the receiving bodies 121 installed therein along any desired track B. The receiving bodies 121 can be held as well by holding devices 125 that are rotatably supported and are aligned as required. The embodiment of the transport device 1 as a linear conveyor should be taken into consideration in particular, if a higher number of loading position, inspection positions and discharge positions need to be provided.

REFERENCES

[1] WO 01/09013 A1
[2] DE19613233A1

The invention claimed is:

1. A method for an optical inspection of workpieces, which are delivered from a loading device to a transport device that is driven by a drive unit and which are transported by the transport device to an inspection device, which performs the optical inspection, and further to a discharge device, which selectively extracts the inspected workpieces depending on a result of the inspection,
   wherein on the transport device a plurality of transparent receiving bodies are firmly mounted or rotatably supported, each of the receiving bodies comprising at least one recess, into which the workpieces are inserted individually or in groups;
   wherein each receiving body is exposed at an inspection position to inspection radiation, which is captured and analysed by the inspection device;
   wherein the receiving bodies are firmly mounted or rotatably supported on a receiving ring, above which a synchronization ring with intake funnels is mounted; and
   wherein the workpieces are cast by the loading device into the intake funnels and drop from the intake funnels each into the recess of the corresponding receiving body.

2. The method according to claim 1, wherein each receiving body is held by a holding device, which is supported in the transport device and which is turned in a plane or in space between at least two positions and is fixed in these positions mechanically or magnetically, so that the receiving bodies take a defined position on at least one loading position, on which the workpieces are delivered from the loading device, on at least one inspection position, on which an optical measurement of the workpieces is performed, and on at least one discharge position, on which the workpieces are selectively removed by the discharge device.

3. The method according to claim 1, wherein the workpieces are continuously forwarded to the synchronization ring and that, without stopping the transport device, the inspection device performs the optical inspection and/or the selective discharge of the workpieces as soon as a marking element is detected.

4. The method according to claim 1, wherein, if alignment is not already provided, each receiving body with a main axis (x) of the recess is aligned with a radius of the receiving ring
   a) in parallel before a loading position is reached, and/or
   b) perpendicularly before the inspection position is reached, and/or
   c) in parallel before a discharge position is reached.

5. An apparatus for an optical inspection of workpieces operating according to the method of claim 1, with a transport device driven by a drive unit, which the transport device can be supplied with the workpieces delivered by a loading device, which the workpieces are transportable by the transport device to at least one inspection position, where the optical inspection is performed by an inspection device, and further to at least one discharge position, where the inspected workpieces are selectively extractable by a discharge device,
   wherein on the transport device a plurality of transparent receiving bodies are firmly mounted or rotatably supported, each of the receiving bodies comprising at least one recess, into which the workpieces can be inserted individually or in groups;
   wherein an inspection radiation can be guided through each receiving body in order to image the held workpieces;
   wherein the receiving bodies are firmly mounted or rotatably supported on a receiving ring, above which a synchronization ring with intake funnels is mounted; and wherein a discharge opening of each intake funnel is arranged above the recess of a corresponding receiving body.

6. The apparatus according to claim 5, wherein at least one of the receiving bodies is a prism, which consists of a single piece or of at least two prisms and which is made from glass or plastic and whose recess comprises a form of a prism having three or more sides.

7. The apparatus according to claim 5, wherein the receiving bodies, which are guided along a closed circular or at least partially linear transport track, are firmly mounted or rotatably supported on the rotatably supported or linearly movable transport device.

8. The apparatus according to claim 7, wherein each receiving body is held by a holding device that is supported in the transport device, and which the holding device is rotatable in a plane or in space between at least two positions, so that the receiving bodies can be turned into a defined position on at least one loading position, on which the workpieces are delivered from the loading device, on at least one inspection position, on which an optical measurement of the workpieces is performed, and on at least one discharge position, on which the workpieces are selectively removed by the discharge device.

9. The apparatus according to claim 8, wherein the holding device comprises a mechanical control element, which engages in such a way with at least one control curve arranged along the transport track that the holding device is rotatable in a defined position or rotatable in a defined position and fixable by means of at least one mechanical or magnetic element.

10. The apparatus according to claim 5, wherein the intake funnels comprise an inclined front side and an inclined back side, which delimit an outlet opening, which is adapted to the recess of the receiving bodies and/or to the workpieces.

11. The apparatus according to claim 5, wherein the receiving ring and the synchronization are separated by distance elements with a clearance in such a way that an interspace is kept free between the receiving ring and the synchronization ring, into which interspace at least a part of the receiving bodies is projecting, which is provided with the recess and through which the inspection radiation is guidable.

12. The apparatus according to claim 5, wherein the transport device comprises a mounting disk that is connected to a drive shaft of the drive unit, which supports the receiving ring and which supports the synchronization ring arranged above the receiving ring.

13. The apparatus according to claim 5, wherein the loading device is a helical conveyer, which delivers the workpieces serially to the synchronisation ring.

14. The apparatus according to claim 5, wherein the inspection device comprises a radiation source, which protrudes into the synchronization ring and which provides the inspection radiation through an interspace radially towards the outside, and which comprises a camera, which captures the inspection radiation exiting out of the interspace.

15. The apparatus according to claim 5, wherein the discharge device comprises pneumatic elements, with which air pressure can be set free at each corresponding discharge position, in order to separate the workpieces, which have been identified as good, bad or undefined, from the receiving bodies.

* * * * *